(12) United States Patent
Glukhovsky

(10) Patent No.: US 7,142,908 B2
(45) Date of Patent: *Nov. 28, 2006

(54) DEVICE AND METHOD FOR MEASUREMENT OF ELECTRICAL CHARACTERISTICS OF TISSUE

(75) Inventor: Arkady Glukhovsky, Santa Clarita, CA (US)

(73) Assignee: Given Imaging Ltd., Yogncam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/440,321

(22) Filed: May 19, 2003

(65) Prior Publication Data

US 2003/0195400 A1 Oct. 16, 2003

Related U.S. Application Data

(63) Continuation of application No. 10/218,164, filed on Aug. 14, 2002, now Pat. No. 6,584,348, which is a continuation of application No. 09/583,275, filed on May 31, 2000, now abandoned.

(51) Int. Cl.
*A61B 5/05* (2006.01)

(52) U.S. Cl. ...................... 600/547; 600/345

(58) Field of Classification Search ................ 600/593, 600/587

See application file for complete search history.

(56) References Cited

U.S. PATENT DOCUMENTS

| | | |
|---|---|---|
| 3,683,389 A | 8/1972 | Hollis |
| 3,971,362 A | 7/1976 | Pope et al. |
| 4,008,712 A | 2/1977 | Nyboer |
| 4,177,800 A | 12/1979 | Enger |
| 4,224,949 A | 9/1980 | Scott et al. |
| 4,278,077 A | 7/1981 | Mizumoto |
| 4,689,621 A | 8/1987 | Kleinberg |
| 4,691,714 A | 9/1987 | Wong et al. |
| 4,741,327 A | 5/1988 | Yabe |
| 4,773,428 A | 9/1988 | Wong et al. |
| 4,784,155 A | 11/1988 | Mills |
| 4,836,214 A | 6/1989 | Sramek |
| 4,844,076 A | 7/1989 | Lesho et al. |
| 4,920,045 A | 4/1990 | Okude et al. |
| 5,109,865 A | 5/1992 | Matsuura |
| 5,109,870 A | 5/1992 | Silny et al. |
| 5,116,119 A | 5/1992 | Brayer |

(Continued)

FOREIGN PATENT DOCUMENTS

DE 29 41 363 4/1981

(Continued)

OTHER PUBLICATIONS

Brown, et al., Applied potential tomography: possible clinical applications, Clin. Phys. Physiol. Meas., 1985, vol. 6, No. 2, 109-121.

(Continued)

*Primary Examiner*—Robert L. Nasser
(74) *Attorney, Agent, or Firm*—Pearl Cohen Zedek Latzer LLP

(57) ABSTRACT

Apparatus for measuring electrical characteristics of biological tissues includes an autonomous capsule with an external surface having openings, a plurality of electrodes located within the openings, and a processor in communication with the plurality of electrodes for generating electrical characteristics. A method for measuring electrical characteristics of biological tissues includes the steps of introducing into the digestive tract an autonomous electrode configuration, selecting sets of electrodes for measurement, introducing a current into the selected electrodes, collecting electrical data from the selected electrodes, and calculating electrical characteristics from the collected data.

28 Claims, 4 Drawing Sheets

U.S. PATENT DOCUMENTS

| | | | |
|---|---|---|---|
| 5,199,433 A * | 4/1993 | Metzger et al. | 600/380 |
| 5,279,607 A | 1/1994 | Schentag et al. | |
| 5,305,745 A * | 4/1994 | Zacouto | 600/324 |
| 5,460,969 A | 10/1995 | Fielder et al. | |
| 5,479,935 A | 1/1996 | Essen-Moller | |
| 5,515,853 A | 5/1996 | Smith et al. | |
| 5,604,531 A | 2/1997 | Iddan et al. | |
| 5,800,350 A | 9/1998 | Coppleson et al. | |
| 5,819,736 A | 10/1998 | Avny et al. | |
| 5,833,603 A * | 11/1998 | Kovacs et al. | 600/317 |
| 5,833,625 A * | 11/1998 | Essen-Moller | 600/547 |
| 5,853,005 A | 12/1998 | Scanlon | |
| 5,882,312 A * | 3/1999 | Gopakumaran et al. | 600/526 |
| 5,928,159 A | 7/1999 | Eggers et al. | |
| 5,932,480 A | 8/1999 | Maruo et al. | |
| 6,053,873 A * | 4/2000 | Govari et al. | 600/505 |
| 6,074,349 A | 6/2000 | Crowley | |
| 6,165,128 A | 12/2000 | Céspedes et al. | |
| 6,240,312 B1 | 5/2001 | Alfano et al. | |
| 6,463,326 B1 * | 10/2002 | Hartley et al. | 607/20 |
| 6,583,348 B1 * | 6/2003 | Hasegawa et al. | 84/609 |
| 6,584,348 B1 * | 6/2003 | Glukhovsky | 600/547 |
| 6,607,301 B1 | 8/2003 | Glukhovsky et al. | |
| 2001/0017649 A1 | 8/2001 | Yaron | |
| 2001/0051766 A1 | 12/2001 | Gazdzinski | |
| 2002/0198439 A1 | 12/2002 | Mizuno | |
| 2003/0018280 A1 | 1/2003 | Lewkowicz et al. | |
| 2003/0040685 A1 | 2/2003 | Lewkowicz et al. | |
| 2003/0195415 A1 | 10/2003 | IdMan | |

FOREIGN PATENT DOCUMENTS

| | | |
|---|---|---|
| DE | 34 40 177 | 5/1986 |
| EP | 0 344 770 | 12/1989 |
| JP | 57-45833 | 3/1982 |
| JP | HEI 3-289779 | 12/1991 |
| JP | 4109927 | 4/1992 |
| JP | HEI 4-109927 | 4/1992 |
| JP | HEI 4-180736 | 6/1992 |
| JP | 5015515 | 1/1993 |
| JP | 2001224553 | 8/2001 |
| WO | WO 92/21307 | 12/1992 |
| WO | WO 98/11816 | 3/1998 |
| WO | WO 00/22975 | 4/2000 |
| WO | WO 01/08548 | 2/2001 |
| WO | WO 01/50941 | 7/2001 |
| WO | WO 01/65995 | 9/2001 |
| WO | WO 02/094337 | 11/2002 |
| WO | PCT/IL03/00982 | 11/2003 |
| WO | WO 03/094723 | 11/2003 |
| WO | PCT/IL03/01080 | 12/2003 |
| WO | WO 2004/004540 | 1/2004 |

OTHER PUBLICATIONS

Casas, et al., In Vivo and In Situ Ischemic Tissue Characterization Using Electrical Impedance Spectroscopy, Annals New York Academy of Sciences, pp. 51-58.

Chauveau, et al., Ex Vivo Discrimination between Normal and Pathological Tissues in Human Breast Surgical Biopsies Using Bioimpedance Spectroscopy, Annals New York Academy of Sciences, pp. 42-50.

Davies, et al, Colonic Epithelial Impedence Analysis in a Murine Model of Large-Bowel Cancer, Arch Surg—vol. 121, Nov. 1986, pp. 1253-1258.

Davies, et al., Detection of the Cancer-Prone Colon, Using Transepithelial Impedence Analysis, Arch Surg—vol. 124, Apr. 1989, pp. 480-484.

Davies, et al., Epithelial Impedance Analysis in Experimentally Induced Colon Cancer, Biophysical Journal, vol. 52, 1987, pp. 783-790.

Frerichs—Monitoring Regional Lung Ventilation by Functional Electrical Impedance Tomography during Assisted Ventilation, Annals New York Academy of Sciences, pp. 493-505.

Fromm, et al., Epithelial and subepithelial contibutions to transmural electrical resistance of intact rat jejunum, in vitro, Pfluger Arch (1985) 405:400-402.

Gonzalez-Correa, et al., Virtual Biopsies in Barrett's Esophagus Using an Impedance Probe, Annals New York Academy of Sciences, vol. 873, Apr. 1999, pp. 313-321.

Gregersen, et al., Impedance Planimetry: A New Approach to Biomechanical Intestinal Wall Properties, Dig Dis 1991;9:332-340.

Jossinet, et al. A hardware design for imaging the electrical impedance of the breast, Clin. Phys. Physiol. Meas., 1988, vol. 9, Suppl. A, pp. 25-28.

Jossinet, Variability of impedivity in normal and pathological breast tissue, Medical and Biological Engineering and Computer, Sep. 1996, pp. 346-350.

Mitsuyama, et al., In Vivo Measurements of Electrical Bio-Impedance of Breast Tumors, p. 255.

Morimoto, et al., A Study of the Electrical Bio-impedance of Tumors, Journal of Investigative Surgery, vol. 6, pp. 25-32.

Morimoto, et al., Measurement of the Electrical Bio-Impedance of Breast Tumors, Eur Surg Res 1990;22:86-92.

Nicander, et al., Electrical impendance. A method to evaluate subtle changes of the human oral mucosa, European Journal of Oral Sciences 1997: 105: 576-582.

Pappenheimer, et al., Transmucosal impedance of small intestine: correlation with transport of sugars and amino acids, 1992—The American Physiological Society.

Paulsen, et al., In Vivo Electrical Impedance Spectroscopic Monitoring of the Progression of Radiation-Induced Tissue Injury, Radiation Research 152, 41-50 (1999).

Schukzke, et al., Epithelial and subepithelial resistance of rat large intestine: segmental differences, effect of stripping, time course, and action of aldosterone, Pflugers Arch (1986) 407: 632-637.

Yasui, et al., Body Composition Analysis of Cachetic Rabbits by Total Body Electrical Conductivity, Nutrition and Cancer, 32(3), 190-193.

The Radio Pill, Rowlands, et al., British Communications and Electronics, Aug. 1960, pp. 598-601.

Video Camera to "TAKE"—RF Systems lab, Dec. 25, 2001.

Wellesley company sends body monitiors into space—Crum, Apr. 1998.

When mammographic findings are equivocal . . . TS2000—TransScan.

Wireless transmission of a color television moving image from the stomach using a miniature CCD camera, light source and microwave transmitter Swain CP, Gong F, Mills TN. Gastrointest Endosc 1997;45:AB40.

BBC News Online—Pill camera to 'broadcast from the gut', Feb. 21, 2000, www.news.bbc.co.uk.

U.S. Appl. No. 10/724,109, Glukhovsky, et al., filed Dec. 1, 2003.

Lehrer, et al., Electrical Resistance of genital tissues during reproductive events in cows, and its possible on-farm applications: A review, Wiener Tierarztliche Monatsschrifft, vol. 78, 1991, pp. 317-322.

www.rfnorkia.com—NORIKA3, Dec. 24, 2001.

Wang, et al., "Integrated Micro-Instrumentation for Dynamic Monitoring of the Gastro-Intestinal Tract", Presented at IEEE Instrumentation and Measurement Technology Conference, May 2002, Anchorage, Ak, USA, www.see.ed.ac.uk/Naa.publications.html.

Roubik, et al., "Reference Microelectrodes Design Evaluation for On-Chip ISFET-Based Microsensors for "in vivo" Blood Measurements".

"Chemical Microsystem", Department of Microelectronics, Faculty of Electrical Engineering Czech Technical University in Prague, Technická 2, CZ-166 27 Prague 6, Czech Republic.

F. Vald's-Perezgasga, et al., "Isfet Applications in Biological Matter: An Overview", downloaded Oct. 27, 2002, www.cinstrum. unam.mx/revista/pdfv4n3/art3.PDF Robots for the future—Shin-ichi, et al., Nov. 29, 2001.

* cited by examiner

DEVICE AND METHOD FOR MEASUREMENT OF ELECTRICAL CHARACTERISTICS OF TISSUE

CROSS REFERENCE

This application is a continuation of U.S. application Ser. No. 10/218,164, entitled "METHOD FOR MEASUREMENT OF ELECTRICAL CHARACTERISTICS OF TISSUE" filed Aug. 14, 2002 now U.S. Pat No. 6,584,348, which in turn is a continuation of U.S. application Ser. No. 09/583,275, entitled "MEASUREMENT OF ELECTRICAL CHARACTERISTICS OF TISSUE" filed May 31, 2000 now abandoned, each of which are incorporated entirely by reference herein.

FIELD OF THE INVENTION

The present invention relates to in-vivo measurement systems in general and specifically to a device for internal measurements of electrical characteristics of a biological lumen.

BACKGROUND OF THE INVENTION

Physiological tissues are typified by specific electrical impedance characteristics. Variance in types of epithelial tissue, for example, may be recognized by differences in electrical characteristics (Gonzales-Correa C A et al., "Virtual biopsies in Barrett's esophagus using an impedance probe", *Annals of NY Academy of Sciences*, Vol. 873, April 1999, pp. 313–321).

Changes of this characteristic impedance can provide essential information about the tissue, and the entire organism. This concept has been the springboard for a great deal of research into predicting pathological conditions, especially cancer (Blad B and Baldetorp B, "Impedance spectra of tumor tissue in comparison with normal tissue: a possible clinical application for electrical impedance tomography", *Physiological Measurements*, Vol. 17 Suppl 4A, November 1996, pp. 105–115). For example, the early detection of colon cancer may be possible by examining differences in electrical properties of surface colonic epithelium (Davies R J et al., "Colonic epithelial impedance analysis in a murine model of large-bowel cancer", *Archives of Surgery*, Vol. 124(4), April 1989, pp. 480–484). These measurements are generally done using an endoscope or a probe with electrodes at the end.

Similarly, breast cancer may be predictable based on impedance differences in normal and pathological tissue (Chauveau N et al., "Ex vivo discrimination between normal and pathological tissues in human breast surgical biopsies using bioimpedance spectroscopy", *Annals of NY Academy of Sciences*, Vol. 873, April 1999, pp. 42–50; and Jossinet J, "A Variability of impedivity in normal and pathological breast tissue, *Medical and Biological Engineering and Computing*, Vol. 34(5), September 1996, pp. 346–350).

Many other conditions may be predictable based on electrical impedance changes. For example, esophagus impedance may be related to Barrett's esophagus, a disorder in which the normal squamous mucosa of the esophagus is replaced by columnar epithelium (Gonzales-Correa C A et al., "Virtual biopsies in Barrett's esophagus using an impedance probe", *Annals of NY Academy of Sciences*, Vol. 873, April 1999, pp. 313–321). Changes in oral impedance may be related to changes in oral mucosa (Nicander B L et al., "Electrical impedance. A method to evaluate subtle changes of the human oral mucosa", *European Journal of Oral Science*, Vol. 105(6), December 1997, pp. 576–582). Other diagnoses using this principle include tissue injury (Paulsen K D et al., "In vivo electrical impedance spectroscopic monitoring of the progression of radiated-induced tissue injury", *Radiation Research*, Vol. 152(1), July 1999, pp. 41–50), lung ventilation (Frerichs I et al., "Monitoring regional lung ventilation by functional electrical impedance tomography during assisted ventilation", *Annals of NY Academy of Sciences*, Vol. 873, April 1999, pp. 493–505), and ischemic tissue (Casa O et al., "In vivo and in situ ischemic tissue characterization using electrical impedance spectroscopy", *Annals of NY Academy of Sciences*, Vol. 873, April 1999, pp. 51–58).

Measurement of impedance characteristics of tissue is typically accomplished through the use of a probe with electrodes or by implanting electrodes (Lehrer A R et al., "Electrical resistance of genital tissues during reproductive events in cows, and its possible on-farm applications: A review", Wiener Tierarztliche Monatsschrift, Vol. 78, 1991, pp. 317–322). The electrodes may be attached to the end of an enteroscope for measurements of the intestines. Additional techniques have been developed as well. One of these techniques is termed "electrical impedance tomography", or EIT (Brown B H et al., "Applied potential tomography: possible clinical applications", *Clinical Physiology and Physiological Measurements*, Vol. 6(2), May 1985, pp. 109–121). This method involves resistivity distribution changes following ingestion of conducting or insulating fluids. In addition, body composition may be analyzed by total body conductivity (Galvard H, et al., "Differences in body composition between female geriatric hip fracture patients and healthy controls: body fat is a more important explanatory factor for the fracture than body weight and lean body mass", *Aging (Milano)*, Vol. 8(24), August 1996, pp. 282–286; and Yasiu T, et al., "Body composition analysis of cachetic rabbits by total body electrical conductivity", *Nutrition and Cancer*, Vol. 32(3), 1998, pp. 190–193).

SUMMARY OF THE INVENTION

The present invention describes apparatus and method for measuring electrical characteristics of a biological lumen.

There is thus provided, in accordance with a preferred embodiment of the present invention, apparatus for measuring electrical characteristics of biological tissues which includes a capsule with an external surface having openings, a plurality of electrodes located within the openings, and a processor in communication with the electrodes for generating electrical characteristics.

The apparatus may further include an imager for imaging an area of interest within the biological tissue.

The capsule may be autonomous, and it may be introduced by swallowing or by placing it in a desired location in the body.

The electrical characteristics may include impedance or conductivity values or any other relevant electrical characteristics as determined by the user. The biological tissue may be the small intestine or the interior of any portion of the digestive tract.

The plurality of electrodes includes at least two electrodes. Electrodes may be metallic rings, where the openings are slits, or they may be metallic spheres or cups, where the openings are round. Electrodes may protrude through the openings or they may be flush with the external surface of the capsule.

The invention further describes a method for measuring electrical characteristics of a digestive tract in a body, including the following steps: introducing into the digestive tract an autonomous electrode configuration, selecting sets of electrodes for measurement, introducing a current into the selected electrodes, collecting electrical data from selected electrodes, and calculating electrical characteristics from collected data. The autonomous configuration may be located on the external surface of a capsule, and it may be introduced into the digestive tract by swallowing.

A further embodiment of the present invention includes the step of transmitting the electrical characteristics to a wireless receiver outside the body.

In one embodiment of the present invention the step of collecting includes obtaining a voltage between the two selected electrodes. Electrical characteristics may be impedance or conductivity values.

Furthermore, one embodiment of the present invention includes the step of measuring a time parameter. Another embodiment further includes the step of determining a distance within the digestive tract.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

The present invention is a capsule with external electrodes. It may be autonomous, in that it moves through the digestive system without external control, and it may be introduced into the body by swallowing or by placing it in a desired location in the body.

In vivo measurement systems which are known in the art typically include swallowable electronic capsules which collect data and which transmit the data to a receiver system. These intestinal capsules, which are moved through the digestive system through the action of peristalsis, are often called "Heidelberg" capsules and are utilized to measure pH, temperature ("Coretemp") and pressure throughout the intestines. They have also been utilized to measure gastric residence time, which is the time it takes for food to pass through the stomach and intestines.

The intestinal capsules typically include a measuring system and a transmission system, where the transmission system transmits the measured data at radio frequencies to the receiver system. The receiver system is usually located outside the body. Alternate systems can store all the data within a storage device in the capsule. The data can then be read after the capsule exits the gastro-intestinal (GI) tract.

Figure 1:
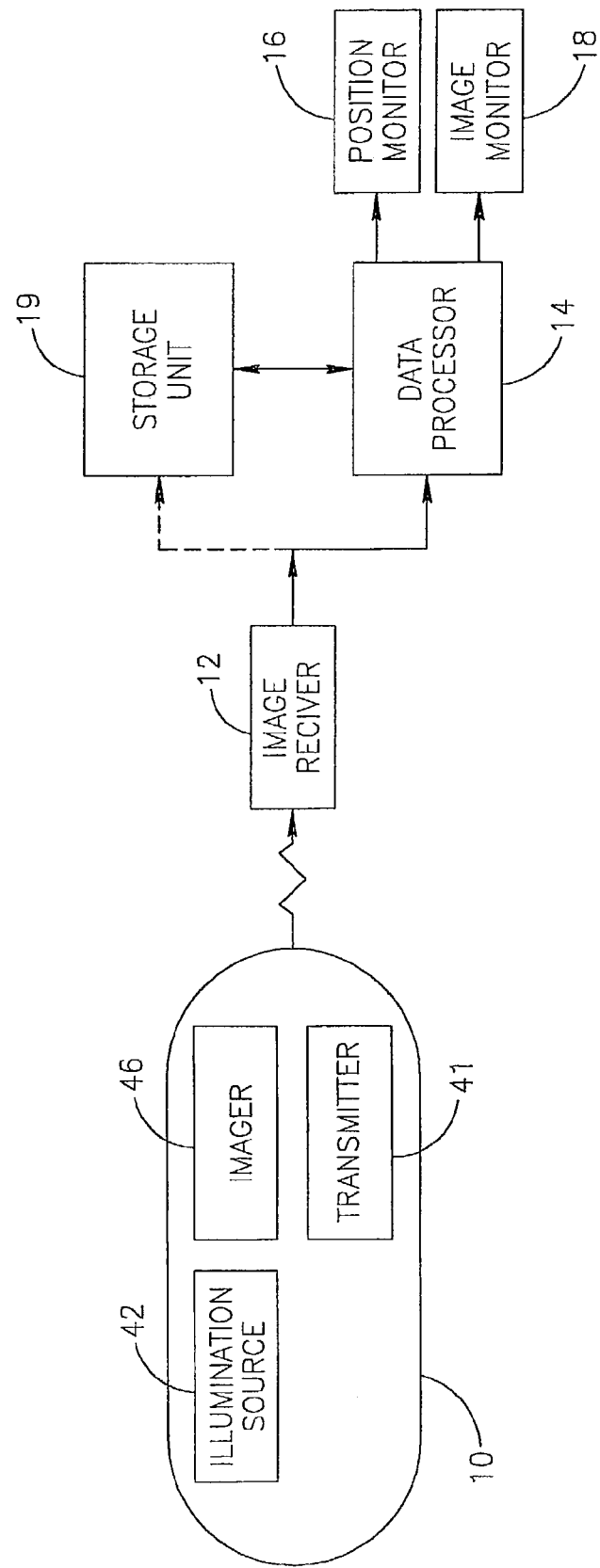
FIG. 1 is a block diagram illustration of a prior art swallowable capsule for video imaging.

In U.S. Pat. No. 5,604,531, which is incorporated herein by reference, the common assignees of the present application describe a swallowable capsule that can pass through the entire digestive tract, including the small intestine, and operate as an autonomous video endoscope. A block diagram of the system of U.S. Pat. No. 5,604,531 is illustrated in FIG. 1.

The in vivo video camera system typically comprises a swallowable capsule 10 for viewing inside the digestive system and for transmitting at least video data, a reception system 12 typically located outside a patient, and a data processor 14 for processing the video data. The data processor 14 typically operates two monitors, a position monitor 16 on which the current location of the capsule 10 within the digestive system is displayed and an image monitor 18 on which the image currently viewed by the capsule 10 is displayed.

The reception system 12 can either be portable, in which case the data it receives is temporarily stored in a storage unit 19 prior to its processing in data processor 14, or it can be stationary and close to the data processor 14. The capsule typically comprises an illumination source 42, an imager 46, and a transmitter 41.

Figure 2A:
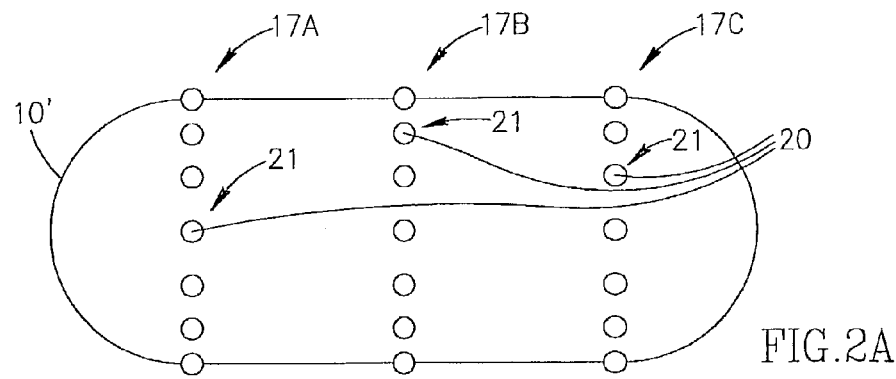
FIGS. 2A, 2B and 2C are schematic illustrations of several embodiments of a capsule of the present invention having electrodes thereon.
Figure 2B:
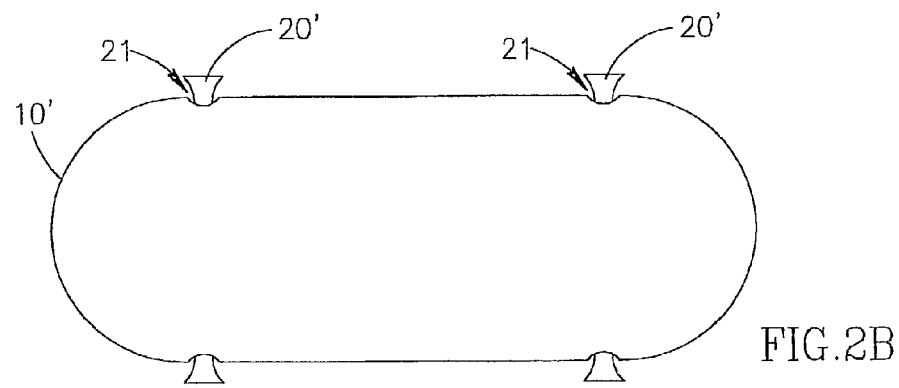
Figure 2C:
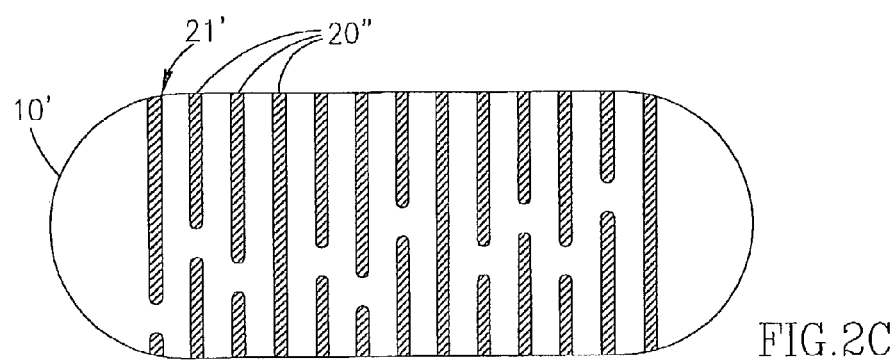

Reference is now made to FIGS. 2A, 2B and 2C, which illustrate several embodiments of a capsule 10' of the present invention having electrodes 20 thereon. It should be noted that the capsule 10' as described with electrodes 20 thereon may or may not additionally comprise the in vivo camera system described above.

The capsule 10' is typically made from plastic material, and is fabricated with small openings 21 for electrodes 20. The electrodes 20 are placed through the openings 21 so that part of each electrode 20 remains within the interior portion of the capsule 10', and part of each electrode 20 protrudes out from the other side of the opening 21. Alternatively, electrodes 20 may be flush with the surface of the capsule 10'. The electrodes 20 may be spherical in shape, or they may be fabricated in other shapes and forms, such as cup-shaped electrodes 20' as in FIG. 2B.

In the configuration illustrated in FIG. 2C, the openings 21' are slits positioned around the capsule 10', within which are located electrodes 20" in the form of metallic rings. In either embodiment, capsules 10' must include a minimum of two electrodes, but may contain many more, in sets of two. Other embodiments are possible as well.

Figure 3:
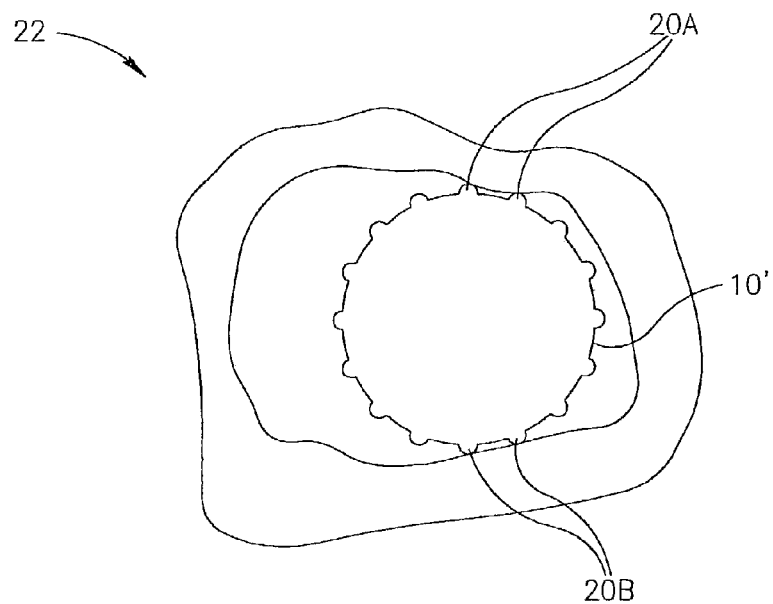
FIG. 3 is a cross section illustration of the capsule of FIG. 2A within the small intestine.
Figure 4:
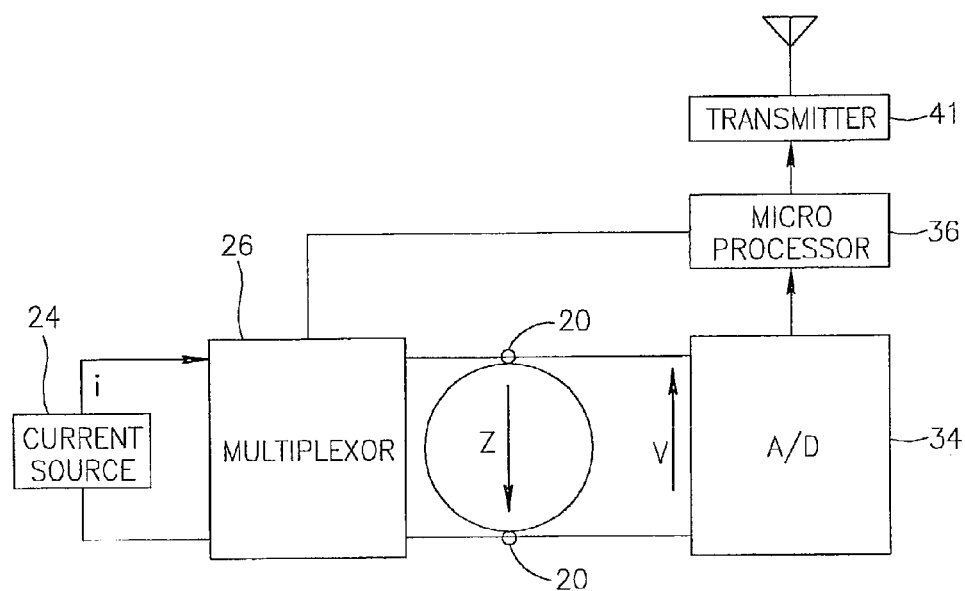
FIG. 4 is a block diagram illustration of impedance measurement and transmission.

Reference is now made to FIGS. 3 and 4. FIG. 3 is a cross section illustration of the capsule 10' with spherical electrodes 20 within the intestine 22 and FIG. 4 is a block diagram illustration of the processing output of the electrodes.

As shown in FIG. 3, at any given point in time, some electrodes will be in contact with the interior portion of the digestive tract, while others will not. Impedance values measured between a pair of electrodes which are in contact with the digestive tract will be much higher than ones not in contact. Thus, as shown in FIG. 4, a multiplexer 26 is used to select a pair of electrodes (for example, 20A or 20B (FIG. 3)) for measurement of electrical potential and calculation of impedance, or conversely, conductivity values.

The circuit of FIG. 4 comprises a current source 24, a multiplexer 26, an analog to digital (A/D) converter 34, a microprocessor 36, and the transmitter 41. Current source 24 sends a known, constant current input through multiplexer 26, which selects a first pair of electrodes 20A. The resulting voltage Voutput is converted by A/D converter 34 and provided to microprocessor 36, which calculates an impedance value therefrom. Impedance Z (expressed in Ohms) is calculated as the normalized ratio of voltage to current according to the following equation:

$$Z = (1/L) * (V_{output}/I_{input})$$

where L is the distance between the selected electrodes.

The multiplexer 26, in direct communication with microprocessor 36, then selects another pair of electrodes 20B for impedance calculations. Every possible combination of electrode pairs is selected. Microprocessor 36 then selects the maximum impedance value from among the electrode pairs and this value is transmitted through transmitter 41 to a receiver located outside the body. The transmitted value is proportional to a characteristic impedance value for the region being measured, and is used for comparison with values obtained from other regions within the digestive tract. A similar method may be employed for other electrode configurations.

Measurements may be made at any point along the digestive tract, although the smaller diameter sections will have more contact with the electrodes. Measurements are taken at periodic intervals, for example every 0.1 second. The location of the capsule within the digestive tract at the time of measurement is determined by a telemetric system, as described in U.S. Pat. No. 5,604,531. Changes in impedance may also signal passage of the capsule through different segments of the digestive tract, such as the pylorus or various organs. For example, differences in pH values along the tract, such as the stomach versus the intestines, will result in changes in impedance measurements. These values may also aid the telemetry system of U.S. Pat. No. 5,604,531 in confirming the location of the capsule 10' along the path of the digestive tract.

Reference is now made back to FIG. 2, which shows electrodes 20 surrounding capsule 10', in rows 17A, 17B and 17C. Rows 17A, 17B and 17C are separated from one another by known distances, and there may be any number of rows of electrodes 20.

Figure 5A:
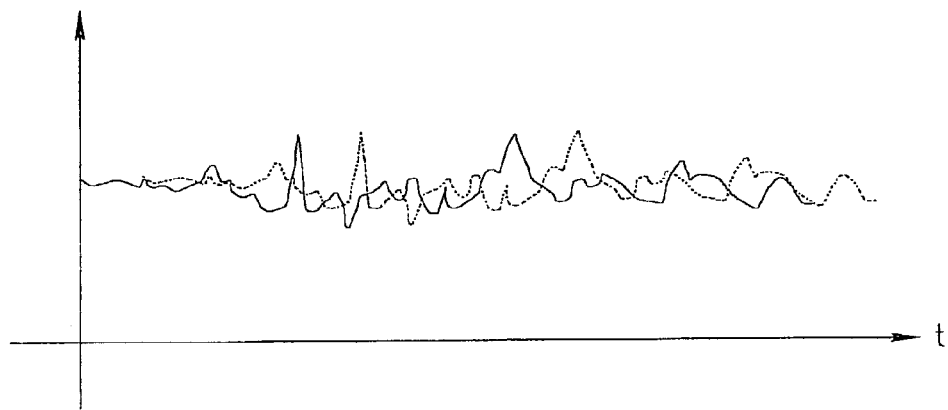
FIG. 5A is a graphical illustration of impedance for two electrodes, useful in understanding the measurement and processing illustrated in FIG. 4.
Figure 5B:
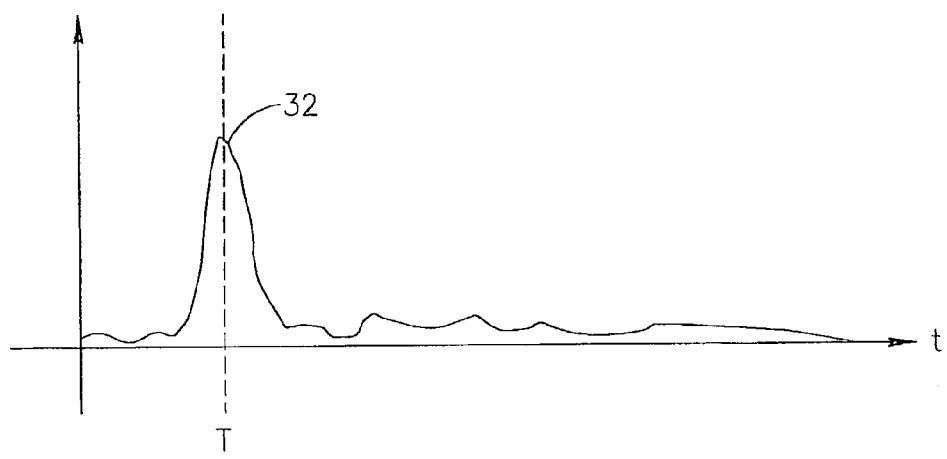
FIG. 5B is a graphical illustration of the correlation of the two traces of FIG. 5A.

Reference is now made to FIGS. 5A and 5B. FIG. 5A shows the impedance values of two sets of electrodes over time, while FIG. 5B illustrates the cross-correlation of the output of the two sets of electrodes. Due to spatial inhomogeneity of the tissues along the path of the capsule, the measured impedance versus time will show some fluctuations. In the graph, the solid line represents the signal obtained from a first pair of electrodes 20 located along a first row 17A (FIG. 2A). The dotted line represents the signal obtained from another pair of electrodes 20 located along a second row 17B (FIG. 2A). Similar measurements may be made from other electrode configurations. The two resulting traces are similar, but there is a time lag between them.

FIG. 5B shows the cross-correlation between the two pairs of electrodes located around the capsule. As can be seen, there is a peak 32 in the graph. This peak occurs at time T and indicates the time it takes for the capsule to travel the distance between the two pairs of electrodes. It should be noted that a minimum of four electrodes are needed for this calculation.

These values can be used to calculate the velocity of the capsule, for example using a method similar to the one described in U.S. Pat. No. 5,116,119, which is incorporated herein by reference. U.S. Pat. No. 5,116,119, entitled "Method and Apparatus for Measuring Liquid Flow", describes a method of measuring liquid flow by electromagnetic radiation within a chamber of known dimensions. The momentary attenuation of the electromagnetic radiation by the liquid is measured so as to determine the momentary volume and velocity of the liquid. Similarly, the present invention utilizes electrical properties to determine velocity.

Other information may also be obtained from the cross-correlation. For example, the length of a segment from some known reference point, such as the pylorus, can be calculated.

It will be appreciated by persons skilled in the art that the present invention is not limited by what has been particularly shown and described herein above. Rather the scope of the invention is defined by the claims which follow:

What is claimed is:

1. A method for measuring electrical impedance of a biological lumen, the method comprising:
   introducing into said biological lumen an autonomous device, said device including a plurality of electrodes;
   collecting electrical data from said plurality of electrodes;
   calculating electrical impedance from said collected data; and
   selecting a maximum impedance value among a plurality of impedance values,
   wherein said introducing of said device is accomplished by swallowing.

2. A method as in claim 1 wherein device is a capsule.

3. A method as in claim 1 further comprising transmitting said calculated electrical impedance to a receiver.

4. A method as in claim 1 wherein said collecting electrical data includes recording a voltage.

5. A method as in claim 1 wherein said calculating electrical impedance further includes calculating conductivity.

6. A method as in claim 1 further comprising measuring a time parameter.

7. A method as in claim 1 further comprising determining a distance within the lumen.

8. The method of claim 1 wherein the plurality of electrodes includes at least four electrodes.

9. A method comprising:
   selecting a pair of electrodes that are in contact with gastrointestinal tract in an autonomous in-vivo device including a plurality of electrodes;
   collecting electrical data from the selected electrodes; and
   selecting a maximum impedance value among a plurality of impedance values.

10. The method of claim 9 wherein said device is a capsule.

11. The method of claim 9 comprising transmitting said data.

12. The method of claim 9 comprising recording a voltage between the selected electrodes.

13. Apparatus for measuring electrical characteristics of biological tissues, comprising:
   a plurality of electrodes; and
   a processor that receives a plurality of impedance values from said electrodes, said impedance values being received from at least two sets of electrodes, wherein the processor selects the a maximum impedance value among said plurality of impedance values, and
   wherein said electrical characteristics include at least conductivity values.

14. The apparatus according to claim 13 further comprising an imager.

15. Apparatus according to claim 13 wherein said device is autonomous.

16. The apparatus according to claim 13 wherein said apparatus is configured to enable said set of electrodes to be in contact with an interior portion of said biological tissue.

17. The apparatus according to claim 13 wherein said apparatus is a capsule.

18. The apparatus according to claim 13 wherein said biological tissue is an interior of any portion of a digestive tract.

19. The apparatus according to claim 13 wherein said plurality of electrodes are selected from a group consisting of: metallic rings, metallic spheres, and cup-shaped electrodes.

20. The apparatus according to claim 13, comprising an external surface having openings; and wherein the plurality of electrodes are located within said openings.

21. The apparatus according to claim 20 wherein said openings are round.

22. The apparatus according to claim 13 wherein said electrodes are flush with an external surface of said apparatus.

23. The apparatus according to claim 13 wherein said electrodes protrude from an external surface of said apparatus.

24. The apparatus according to claim 13 wherein said processor comprises a multiplexer said multiplexer configured to select the set of electrodes.

25. The apparatus according to claim 13 wherein said processor comprises a microprocessor said microprocessor is configured to select a maximum value.

26. The apparatus according to claim 13 wherein said processor is configured to calculate impedance between said selected electrodes.

27. The apparatus according to claim 13 wherein said processor is configured to further calculate conductivity.

28. The apparatus according to claim 13 wherein said processor is configured to further determine a distance within a digestive tract.

* * * * *